United States Patent [19]
Heveling et al.

[11] Patent Number: 5,917,051
[45] Date of Patent: Jun. 29, 1999

[54] PROCESS FOR THE PREPARATION OF FORMYLIMIDAZOLES

[75] Inventors: Josef Heveling, Naters; Alain Wellig, Kanton Wallis, both of Switzerland

[73] Assignee: Lonza, AG, Gampel/Valais, Switzerland

[21] Appl. No.: 09/176,935

[22] Filed: Oct. 23, 1998

[30] Foreign Application Priority Data

Oct. 29, 1997 [CH] Switzerland .............................. 2504/97

[51] Int. Cl.$^6$ ........................ C07D 233/68; C07D 233/96
[52] U.S. Cl. .......................................................... 548/333.5
[58] Field of Search .......................................... 548/333.5

[56] References Cited

U.S. PATENT DOCUMENTS 5,336,779  8/1994  Yamamoto et al. .................. 548/333.5

FOREIGN PATENT DOCUMENTS 685496  7/1995  Switzerland .
WO 92/20651  5/1992  WIPO .

OTHER PUBLICATIONS

E.F. Godefrol et al., Trav. Chim. Receuil Pays–Bas, 91, 1383, (1972).

*Primary Examiner*—Patricia L. Morris
*Attorney, Agent, or Firm*—Fisher, Christen & Sabol

[57] ABSTRACT

A process for the catalytic conversion of halogenated hydroxymethylimidazoles to halogenated formylimidazoles. The catalysis takes place in the presence of a peroxide. Halogenated formylimidazoles are important intermediates for pharmaceutical active ingredients.

14 Claims, No Drawings

PROCESS FOR THE PREPARATION OF FORMYLIMIDAZOLES

BACKGROUND OF THE INVENTION

1. Field Of The Invention

The invention relates to a novel process for the preparation of formylimidazoles of the general formula:

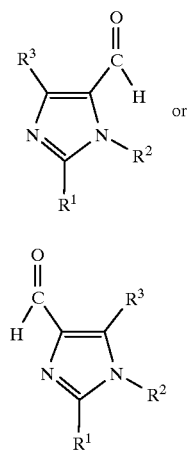

in which $R^1$ is hydrogen or an alkyl group, $R^2$ is hydrogen, an alkyl group, an aryl group or an arylalkyl group, and $R^3$ is halogen, by catalytic oxidation of hydroxymethylimidazoles of the general formula:

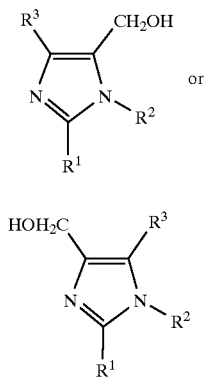

in which $R^1$, $R^2$ and $R^3$ are as defined above.

2. Background Art

Formylimidazoles are important intermediates, for example, for the preparation of pharmaceutical active ingredients, such as, diuretics or antihypertensives (International Published Patent Application No. WO-A 92/20651). Several processes for the preparation of formylimidazoles are know to date. Swiss Patent No. 685, 496 describes a process in which the catalytic oxidation of hydroxymethylimidazoles to formylimidazoles is carried out in the presence of noble-metal catalysts, such as, platinum-bismuth, platinum black, platinum or palladium on activated carbon, while passing in oxygen. Disadvantages of such process are the long reaction times of several hours and the formation of by-products.

BROAD DESCRIPTION OF THE INVENTION

The object of the invention is to provide an economical process for the preparation of formylimidazoles which does not have the above-mentioned disadvantages. This object is achieved by the process according to the invention.

Other objects and advantages of the invention are set out herein or are obvious herefrom to one skilled in the art. These objects and advantages are achieved by the process of the invention.

Hydroxymethylimidazoles of the general formula:

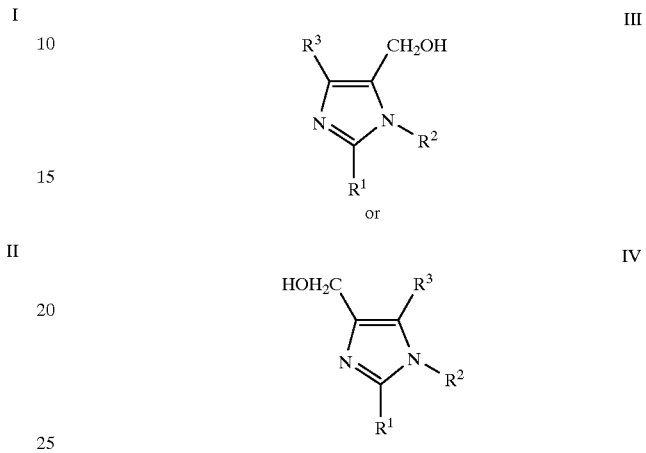

in which $R^1$, $R^2$ and $R^3$ are as defined above, are catalytically oxidized in the presence of a noble-metal catalyst and a peroxide to formylimidazoles of the general formula:

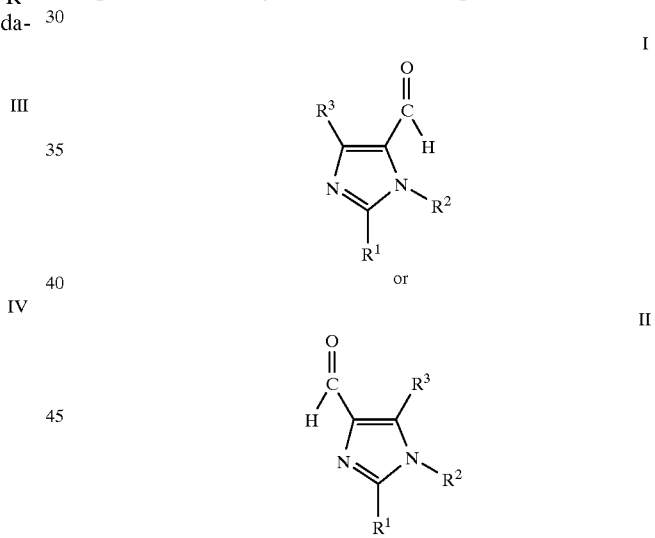

in which $R^1$, $R^2$ and $R^3$ are as defined above.

$R^1$ and $R^2$ independently of one another are hydrogen or an alkyl group, in particular a straight-chain or branched, optionally substituted alkyl group having from 1 to 6 carbon atoms. Examples of the alkyl group are methyl, ethyl, propyl, isopropyl, butyl, isobutyl, tert-butyl, pentyl and its isomers and also hexyl and its isomers. $R^2$ can also be aryl or arylalkyl, in particular optionally substituted phenyl or phenylalkyl. Phenylalkyl is advantageously taken to mean phenyl $C_{1-6}$-alkyl, preferably benzyl. Expedient substituents of the alkyl groups or of the aromatic system of the aryl function are, for example, halogen, amino, alkylamino, dialkylamino, alkoxy or hydroxyl. Halogen as used here and elsewhere herein is taken to mean fluorine, chlorine, bromine or iodine. In particularly preferred meanings, $R^1$ is butyl, and $R^2$ is hydrogen.

$R^3$ is halogen, preferably chlorine.

DETAILED DESCRIPTION OF THE INVENTION

The starting compounds hydroxymethylimidazoles can be prepared in a simple manner, for example, according to the procedure in International Published Patent Application No. WO-A 92/20651 or according to E. F. Godefrol et al., Trav. Chim. Receuil Pays-Bas, 91, 1383, (1972).

The noble-metal catalyst can be platinum, palladium, rhodium or gold. The noble metal is expediently used in combination with metals, such as, bismuth, lead, cerium or indium as a second component. Preference is given to platinum/bismuth or platinum/lead catalysts.

The noble-metal catalyst is used as such or bonded to a support material, such as, activated carbon, silicon dioxide, aluminum dioxide, silicon aluminum dioxide, zirconium oxide or titanium oxide. It is preferably bonded to activated carbon. Noble-metal catalysts which are bonded to activated carbon are available commercially, for example, from Degussa. The amount of noble metal bonded to a support material is expediently between 0.1 and 15 percent by weight, preferably between 0.5 and 7 percent by weight, based on the support material.

The noble-metal catalyst is preferably used in an amount of from 0.05 to 1.0 mol percent based on noble metal, relative to the hydroxymethylimidazole of the general formula III or IV, and particularly preferably in an amount of from 0.1 to 0.4 mol percent based on noble metal, relative to the hydroxymethylimidazole of the general formula III or IV.

The peroxides used are organic or inorganic peroxides. Examples of suitable peroxides are hydrogen peroxide, perborates, a percarboxylic acid, tert-butyl hydroperoxide, cumene hydroperoxide, perbenzoic acid, m-chloroperbenzoic acid, monoperphthalic acid or peracetic acid. A particularly suitable peroxide is hydrogen peroxide, which is advantageously used as a 10 to 30 percent strength aqueous solution.

The catalytic oxidation expediently takes place in the presence of water, a water-miscible polar solvent, a water-immiscible nonpolar solvent or mixtures thereof, in an alkaline medium. Examples of suitable water-miscible polar solvents are alcohols or carboxylic acids having from 1 to 6 carbon atoms, or ketones, such as, acetone or methyl ethyl ketone. Examples of suitable water-immiscible nonpolar solvents are isobutyl methyl ketone or ethyl acetate.

Mixtures of water and water-miscible polar solvent, preferably an alcohol, particularly preferably methanol, are advantageously used. Mixtures of water and a water-immiscible nonpolar solvent, particularly preferably isobutyl methyl ketone, are likewise advantageously used. It has been found advantageous to produce the alkaline medium by adding an alkali metal hydroxide, an alkali metal carbonate or an alkali metal acetate to the reaction mixture. Alkali metal hydroxide is preferably used in the ratio from 1:0.05 to 1.2, preferably from 1:0.1 to 1, based on the molar amount used of the hydroxymethylimidazole of the general formula III or IV.

The catalytic oxidation expediently takes place at a temperature of 20° to 120°, advantageously at 50° to 80° C.

After a customary peroxide metering time of approximately 1 hour, it is possible, after a sufficient post-reaction time, to isolate the compound of the general formula I or II in a manner customary to the person skilled in the art.

The product is expediently isolated, depending on the solvent system, either by crystallization and filtration or by extraction with a suitable solvent. The catalyst used can be used repeatedly without loss of activity.

EXAMPLE 1

Process for the preparation of 2-n-butyl-4-chloro-5-formylimidazole 4.0 g of 2-n-butyl4-chloro-5-hydroxymethylimidazole, 21.5 ml of 1N NaOH and 13.6 ml of methanol were heated to 60° C. to give a solution. 0.6 g of 5% Pt-5% Bi/C (Degussa, comprising 60 percent $H_2O$) was added. At 60° to 62° C., 4.2 g of 20 percent strength aqueous $H_2O_2$ solution was added dropwise over 60 min. The mixture was then left to react for a further 15 min; it was then filtered, and the catalyst was then washed with 5 ml of methanol. The filtrate was adjusted from pH 12.4 to pH 7.5 using 32 percent strength HCl. 15 ml of $H_2O$ was added, and the mixture was partially evaporated on a rotary evaporator (removal of methanol). The mixture was then allowed to cool with thorough stirring, and the resultant white suspension was filtered at 20° C. The filter cake was then washed with 5 ml of $H_2O$ and dried to give 3.4 g of a white to slightly yellowish substance. According to $^1$H NMR, this substance comprised 32.6 mol percent of 2-n-butyl4-chloro-5-hydroxymethylimidazole and 67.3 mol percent of 2-n-butyl4-chloro-5-formylimidazole. $^1$H NMR data for 2-n-butyl4-chloro-5-formylimidazole was:

$^1$H NMR (DMSO-$_{d16}$, 400 MHz) δ:    13.3 (1 H, bs);
                                         9.6 (1 H, s);
                                         2.64 (2 H, t);
                                         1.63 (2 H, m);
                                         1.27 (2 H, m);
                                         0.88 (3 H, t).

EXAMPLE 2

Process for the preparation of 2-n-butyl 4-chloro-5-formylimidazole 4.0 g of 2-n-butyl4-chloro-5-hydroxymethylimidazole, 4 ml of 1N NaOH, 6 ml of $H_2O$ and 12.6 ml of methanol were heated to 60° C. to give a solution. 0.6 g of 5% Pt-5% Bi/C (Degussa, comprising 60 percent $H_2O$) was added. At 60° to 62° C., 4.2 g of 20 percent strength aqueous $H_2O_2$ solution was added dropwise over 60 min. The mixture was then left to react for a further 15 min; it was then filtered, and the catalyst was then washed with 5 ml of methanol. The filtrate was adjusted from pH 8.4 to pH 7.5 using 32 percent strength HCl. 15 ml of $H_2O$ was added, and the mixture was partially evaporated on a rotary evaporator (removal of methanol). The mixture was then allowed to cool with thorough stirring, and the resultant white suspension was filtered at 20° C. The filter cake was then washed with 5 ml of $H_2O$ and dried to give 3.7 g of a white substance. According to $^1$H NMR, this substance comprised 36.9 mol percent of 2-n-butyl4-chloro-5hydroxymethylimidazole and 63.1 mol percent of 2-n-butyl-4-chloro-5-formylimidazole.

EXAMPLE 3

Process for the preparation of 2-n-butyl-4-chloro-5-formylimidazole 3.0 g of 2-n-butyl4-chloro-5-hydroxymethylimidazole, 1.2 g of 5% Pt-5% Bi/C (Degussa, comprising 60% $H_2O$), 44 g of methyl isobutyl ketone, 1.3 ml of 1N NaOH solution and 6.8 g of water were heated to 59° C. with stirring. At 60° to 62° C, 4.0 g of 20 percent strength aqueous $H_2O_2$ solution was added over 75 min. The reaction mixture was then allowed to react for a further 15 min; it was then filtered. The filtrate was adjusted from pH 10.4 to pH 7.0 using 10 percent strength HCl. The mixture was then introduced to a separating funnel, and the aqueous phase was separated off and then extracted with 10 ml of methyl isobutyl ketone. The two organic phases were combined and evaporated on a rotary evaporator. The evaporation residue was 3.1 g of white crystals. According to $^1$H MNR, 93.5 mol percent of 2-n-butyl-4-chloro-5-formylimidazole and 6.5 mol percent of 2-n-butyl-4-chloro-5-hydroxymethylimidazole were obtained.

What is claimed is:

1. A process for the preparation of a formylimidazole of the formula:

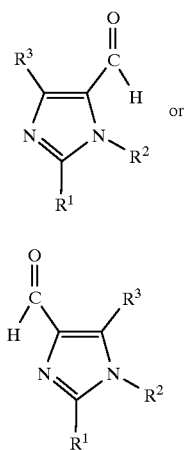

in which $R^1$ is hydrogen or an alkyl group, $R^2$ is hydrogen, an alkyl group, an aryl group or an arylalkyl group, and $R^3$ is halogen, comprising catalytically oxidating a hyroxymethylimidazole of the formula:

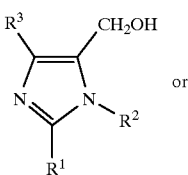

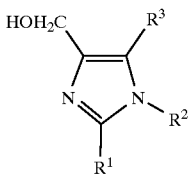

in which $R^1$, $R^2$ and $R^3$ are as defined above, in the presence of a noble-metal catalyst and in the presence of a peroxide.

2. The process according to claim 1, wherein $R^1$ is a butyl group.

3. The process according to claim 2, wherein $R^2$ is hydrogen.

4. The process according to claim 3, wherein the noble-metal catalyst is a platinum/bismuth catalyst or a platinum/lead catalyst.

5. The process according to claim 4, wherein the peroxide is hydrogen peroxide.

6. The process according to claim 5, wherein the catalytic oxidation is carried out in the presence of water, a water-miscible polar solvent, a water-immiscible nonpolar solvent or mixtures thereof, in an alkaline medium.

7. The process according to claim 6, wherein the alkaline medium is obtained by adding an alkali metal hydroxide, alkali metal carbonate or alkali metal acetate to the reaction mixture.

8. The process according to claim 7, wherein the reaction is carried out at a temperature of 20° to 120° C.

9. The process according to claim 1, wherein $R^2$ is hydrogen.

10. The process according to clam 1, wherein the noble-metal catalyst is a platinum/bismuth catalyst or a platinum/lead catalyst.

11. The process according to claim 1, wherein the peroxide is hydrogen peroxide.

12. The process according to claim 1, wherein the catalytic oxidation is carried out in the presence of water, a water-miscible polar solvent, a water-immiscible nonpolar solvent or mixtures thereof, in an alkaline medium.

13. The process according to claim 12, wherein the alkaline medium is obtained by adding an alkali metal hydroxide, alkali metal carbonate or alkali metal acetate to the reaction mixture.

14. The process according to claim 1, wherein the reaction is carried out at a temperature of 20° to 120° C.

* * * * *